United States Patent [19]

Lesher et al.

[11] 4,335,132

[45] Jun. 15, 1982

[54] 5-(PY-Y)-1H-BENZIMIDAZOL-2-OLS AND 5-(PY-Y-)-1H-BENZIMIDAZOLE-2-THIOLS

[75] Inventors: George Y. Lesher, Schodack; Baldev Singh, East Greenbush, both of N.Y.

[73] Assignee: Sterling Drug, Inc., New York, N.Y.

[21] Appl. No.: 220,977

[22] Filed: Dec. 29, 1980

[51] Int. Cl.$^3$ .................. A61K 31/46; C07D 487/02
[52] U.S. Cl. ............................. 424/263; 546/271; 548/305
[58] Field of Search .................. 546/271; 424/263; 548/305

[56] References Cited

U.S. PATENT DOCUMENTS

| | | | |
|---|---|---|---|
| 3,338,916 | 8/1967 | Hunziker | 548/305 |
| 3,842,098 | 10/1974 | Scherhag et al. | 548/305 |
| 3,907,822 | 9/1975 | Narayanan | 548/305 |
| 3,914,310 | 10/1975 | Frick et al. | 548/305 |
| 3,920,683 | 11/1975 | Porret et al. | 548/305 |
| 4,026,936 | 5/1977 | Lauer et al. | 546/271 |

OTHER PUBLICATIONS

Chemical Abstracts, vol. 77, abst. No. 141,468k (1972), (abst. of Zubarovakii et al., Khim Geterotskl. Soedin, 1972 (5), pp. 687–690 (Russ.).

*Primary Examiner*—Henry R. Jiles
*Assistant Examiner*—Robert C. Whittenbaugh
*Attorney, Agent, or Firm*—Robert K. Bair; B. Woodrow Wyatt

[57] ABSTRACT

5-(Py-Y)-1H-benzimidazol-2-ol or 5-(Py-Y)-1H-benzimidazole-2-thiol or lower-alkyl ethers or thioethers thereof or pharmaceutically-acceptable acid-addition salts thereof, useful as cardiotonics, are prepared by reacting 4-(Py-Y)-1,2-benzenediamine with urear or carbonyldiimidazole to produce 5-(Py-Y)-1H-benzimidazol-2-ol or with thiourea, an alkali metal lower-alkyl xanthate or thiocarbonyldiimidazole to produce 5-(Py-Y)-1H-benzimidazole-2-thiol and by reacting 5-(Py-Y)-1H-benzimidazole-2-thiol with a lower-alkylating agent to produce 2-(lower-alkylthio)-5-(Py-Y)-1H-benzimidazole. 2-(Lower-alkoxy)-5-(Py-Y)-1H-benzimidazole is prepared by reacting 4-(Py-Y)-1,2-benzenediamine with tetra-(lower-alkoxy)methane.

12 Claims, No Drawings

5-(PY-Y)-1H-BENZIMIDAZOL-2-OLS AND 5-(PY-Y-)-1H-BENZIMIDAZOLE-2-THIOLS

CROSS-REFERENCE TO RELATED APPLICATION

An intermediate used herein, namely, 4-(3,4-diaminophenyl)pyridine or salt thereof, its preparation and its use as a cardiotonic agent are disclosed and claimed in copending application Ser. No. 173,003, filed July 28, 1980, a continuation-in-part of application Ser. No. 40,210, filed May 18, 1979 and now abandoned.

BACKGROUND OF THE INVENTION (a) Field of the Invention

This invention relates to (pyridinyl)-Y-benzimidazol-2-ols, -2-thiols and lower-alkyl ethers derivatives thereof, their preparation and their use as cardiotonic agents, where Y is a direct linkage or lower-alkylene.

(b) Description of the Prior Art

Zubarovakii et al. [(Inst. Org. Khim., Kiev, USSR) Khim. Geterotsikl. Soedin. 1972, (5), 687–90 (Russ.); C.A. 77, 141,468k (1972)], in a paper entitled "Synthesis of Benzimidazole Derivatives. V. Pyridylbenzimidazoles and Cyanine Dyes From Them" disclose, inter alia, the monohydrochloride of 2-methyl-5-(2-pyridinyl)-1H-benzimidazole, 1-ethyl-2-methyl-5-(2-pyridinyl)-1H-benzimidazole and 2-methyl-1-(2-pyridinyl)-1H-benzimidazole, all as intermediates for preparing cyanine dyes.

The abstract of Lauer and Walser U.S. Pat. No. 4,026,936, issued May 31, 1977, discloses "compounds represented by the formula

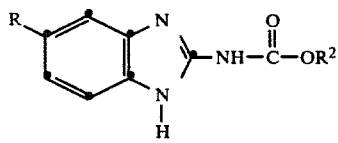

wherein R is

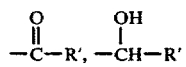

or —(CH₂)ₙ—R', R' is 2-pyridyl, 3-pyridyl, 4-pyridyl or 2-thiazyl, R² is lower alkyl and n is 1 or 2, and acid addition salts of the compounds wherein R' is 2-pyridyl, 3-pyridyl or 4-pyridyl are disclosed as useful as anthelmintics against a broad spectrum of helminths." Specifically disclosed as Example 36 (column 16, lines 47–67) is methyl [5(6)-2-pyridinylmethyl)-2-benzimidazolyl]-carbamate.

SUMMARY OF THE INVENTION

In a composition of matter aspect, the invention resides in 5-(Py-Y)-1H-benzimidazol-2-ol, 5-(Py-Y)-1H-benzimadazole-2-thiol or lower-alkyl ether or thioether derivative thereof or pharmaceutically-acceptable acid-addition salt thereof, which are useful as cardiotonic agents, where Py and Y are defined hereinbelow.

A composition aspect of the invention resides in a cardiotonic composition for increasing cardiac contractility in a patient, said composition comprising a pharmaceutically-acceptable carrier and, as the active ingredient thereof, a cardiotonically-effective amount of 5-(Py-Y)-1H-benzimidazol-2-ol, 5-(Py-Y)-1H-benzimidazole-2-thiol or lower-alkyl ether or thioether derivative thereof or pharmaceutically-acceptable acid-addition salt thereof.

In a method aspect, the invention resides in a method for increasing cardiac contractility in a patient requiring such treatment which comprises the administration of a medicament comprising a pharmaceutically-acceptable carrier and, as the active component thereof, a cardiotonically-effective amount of 5-(Py-Y)-1H-benzimidazol-2-ol, 5-(Py-Y)-1H-benzimidazole-2-thiol or lower-alkyl ether or thioether derivative thereof or pharmaceutically-acceptable acid-addition salt thereof.

The invention in a process aspect comprises reacting 4-(Py-Y)-1,2-benzenediamine with urea or carbonyldiimidazole to produce 5-(Py-Y)-1H-benzimidazol-2-ol or with thiourea, an alkali metal lower-alkyl xanthate or thiocarbonyldiimidazole to produce 5-(Py-Y)-1H-benzimidazole-2-thiol.

Another process aspect of the invention comprises the further step, either alone or in combination of abovesaid process aspect, of reacting 5-(Py-Y)-1H-benzimidazole-2-thiol with a lower-alkylating agent to produce 2-(lower-alkylthio)-5-(Py-Y)-1H-benzimidazole.

In another process aspect of the invention 4-(Py-Y)-1,2-benzenediamine is reacted directly with tetra-(lower-alkoxy)methane to produce 2-(lower-alkoxy)-5-(Py-Y)-1H-benzimidazole.

DETAILED DESCRIPTION INCLUSIVE OF PREFERRED EMBODIMENTS

In a composition of matter aspect the invention resides in a 5-(Py-Y)-1H-benzimidazol-2-ol or 5-(Py-Y)-1H-benzimidazole-2-thiol or lower-alkyl ether or thioether thereof having formula I

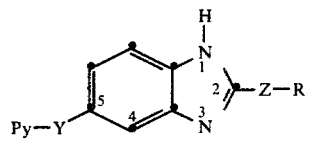

where Z is O or S, Y is a direct linkage or lower-alkylene having one or two carbon atoms, R is hydrogen or lower-alkyl, and Py is 4- or 3-pyridinyl or 4- or 3-pyridinyl having one or two lower-alkyl substituents or 1-oxide thereof, or pharmaceutically-acceptable acid-addition salts thereof. The compounds of formula I are useful as cardiotonic agents, as determined by standard pharmacological evaluation procedures. Preferred embodiments are those of formula I where Py is 4-pyridinyl or 3-pyridinyl, Z is O or S, Y is a direct linkage or methylene, and R is hydrogen, methyl or ethyl.

The compound of formula I where R is hydrogen may exist in tautomeric forms, that is, as 5-(Py-Y)-1H-benzimidazol-2-ol or 5-(Py-Y)-1H-benzimidazole-2-thiol of formula I or as 1,3-dihydro-5(or 6)-(Py-Y)-benzimidazol-2-one or 1,3-dihydro-5(or 6)-(Py-Y)-benzimidazole-2-thione of formula IA or as 6-(Py-Y)-1H-benzimidazol-2-ol or 6-(Py-Y)-1H-benzimidazole-2-thiol of formula IB, illustrated as follows

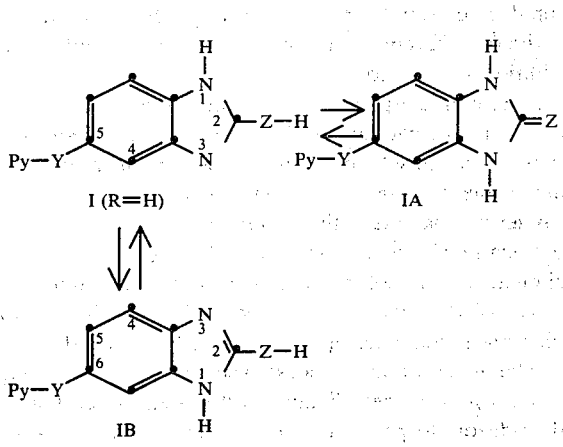

Although in the instant application we have preferred to use the names based on structure I, it is understood in the above instance where R is hydrogen that any one or all three of the structures I, IA and IB are comprehended herein.

A composition aspect of the invention resides in a cardiotonic composition for increasing cardiac contractility, said composition comprising a pharmaceutically-acceptable carrier and, as the active component thereof, a cardiotonically-effective amount of 5-(Py-Y)-1H-benzimidazol-2-ol or 5-(Py-Y)-1H-benzimidazole-2-thiol or lower-alkyl ether or thioether thereof of formula I where Py-Y, Z and R are each defined as in formula I, or pharmaceutically-acceptable acid-addition salt thereof, Preferred embodiments are those having as active components the above-said preferred embodiments of formula I.

A method aspect of the invention resides in the method for increasing cardiac contractility in a patient requiring such treatment which comprises administering orally or parenterally in a solid or liquid dosage form to such patient a medicament comprising a pharmaceutically-acceptable carrier and, as the active component thereof, a cardiotonically-effective amount of 5-(Py-Y)-1H-benzimidazol-2-ol, 5-(Py-Y)-1H-benzimidazole-2-thiol or lower-alkyl ether or thioether thereof of formula I where Py, Y, Z and R are each defined as in formula I, or pharmaceutically-acceptable acid-addition salt thereof. Preferred embodiments are those using as active components the preferred embodiments of formula I.

In a process aspect the invention resides in the process which comprises reacting 4-(Py-Y)-1,2-benzenediamine with urea or carbonyldiimidazole to produce 5-(Py-Y)-1H-benzimidazol-2-ol or with thiourea, an alkali metal lower-alkyl xanthate or thiocarbonyldiimidazole to produce 5-(Py-Y)-1H-benzimidazole-2-thiol. Preferred embodiments of this process aspect are those which produce said preferred composition of matter aspects of formula I where R is hydrogen.

Another process aspect of the invention comprises the further step, either alone or in combination the above-said process aspect, of reacting 5-(Py-Y)-1H-benzimidazole-2-thiol with a lower-alkylating agent to produce 2-(lower-alkylthio)-5-(Py-Y)-1H-benzimidazole of formula I where R is lower-alkyl and Z is S. Preferred embodiments of this process aspect are those which produce said preferred composition of matter embodiments of formula I where R is methyl or ethyl and Z is S.

In another process aspect of the invention 4-(Py-Y)-1,2-benzenediamine is reacted directly with tetra-(lower-alkoxy)methane to produce 2-(lower-alkoxy)-5-(Py-Y)-1H-benzimidazole. Preferred embodiments of this process aspect are those which produce said preferred composition of matter embodiments of formula I where R is methyl or ethyl and Z is O.

The term "lower-alkyl" as used herein, e.g., as one of the meanings for R in formula I or as a substituent for Py in formula I, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of Py in formula I where Py is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term lower-alkylene as used herein, e.g., as one of the meanings for Y in formula I means lower-alkylene radicals having one or two carbon atoms, illustrated by —CH$_2$—, —CH$_2$CH$_2$— or

—CH(CH$_3$).

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salt whose anions are relatively innocuous to the animal organism in pharmaceutical doses of the salts, so that the beneficial cardiotonic properties inherent in the free base (I) are not vitiated by side effects ascribable to the anions. In practicing the invention, it is convenient to use the free base form, the hydrochloride or the methanesulfonate salt; however, appropriate pharmaceutically-acceptable salts within the scope of the invention are those derived from other mineral acids such as hydrobromic acid, sulfuric acid, phosphoric acid and sulfamic acid; and organic acids such as acetic acid, citric acid, lactic acid, tartaric acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, lactate, tartrate, ethanesulfonate, benzenesulfonate, cyclohexylsulfamate and quinate, respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I) are preferred, all acid-addition salts are within the scope of the invention. All acid-addition salts are useful as sources of the free base form even if the particular salt per se is desired only as an intermediate product as for example when the salt is formed only for purposes of purification or identification, or when it is used an an intermediate in preparing a pharmaceutically-acceptable salt by ion exchange procedures.

The molecular structure of the compound of formula I was assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same, as follows.

The preparation of 5-(Py-Y)-1H-benzimidazol-2-ol (I, Z is O and R is H) by reacting 4-(Py-Y)-1,2-benzenediamine with urea is conveniently and preferably carried out by heating the reactants in refluxing dimethylformamide. Alternatively, other suitable inert solvents can be used, e.g., dioxane, nitrobenzene. The reaction using carbonyldiimidazole instead of urea can be run in a suitable solvent, e.g., dimethylformamide at about 35° C. to 80° C. This preparation is illustrated further hereinbelow in Examples B-1 and B-3 through B-10.

The preparation of 5-(Py-Y)-1H-benzimidazole-2-thiol (I, Z is S and R is H) is carried out by reacting 4-(Py-Y)-1,2-benzenediamine with an alkali metal xanthate, thiourea or thiocarbonyldiimidazole. The reaction using an alkali metal xanthate, preferably sodium or potassium salt, is conveniently run by refluxing the reactants in a mixture of water and a lower-alkanol, preferably aqueous ethanol. The reaction using thiourea is conveniently run by heating the reactants in refluxing dimethylformamide or other suitable solvent inert under the reaction conditions. The reaction using thiocarbonyldiimidazole is conveniently run at room temperature or above (up to about 40° C. to 75° C.) in a suitable solvent, preferably dimethylformamide. This preparation is further illustrated below in Examples C-1 through C-9.

The preparation of the compounds of formula I where Py is Py-1-oxide are prepared by treating I or precursor thereof containing Py with a per-organic acid in a suitable solvent, preferably peracetic acid or m-chloroperoxybenzoic acid in acetic acid, at about 40° to 60° C., preferably about 45°-50° C. This oxidation is illustrated further hereinbelow in Example B-2.

The preparation of 2-(lower-alkoxy)-5-(Py-Y)-1H-benzimidazole by reacting 4-(Py-Y)-1,2-benzenediamine with tetra-(lower-alkoxy)methane is carried out by mixing the reactants in a suitable solvent, e.g., acetic acid, and then heating the reaction mixture at about 75° to 125° C., preferably about 90° to 110° C. This reaction is illustrated below in Examples D-1 through D-13.

The reaction of 5-(Py-Y)-1H-benzimidazole-2-thiol, preferably as its alkali metal salt, with a lower-alkylating agent, preferably a lower-alkyl ester of a strong inorganic acid or an organic sulfonic acid, is conveniently run by mixing the reactants in a suitable solvent, e.g., aqueous ethanol, at room temperature or at about 40° to 60° C. if necessary to facilitate the reaction. This preparation is illustrated below in Examples E-1 through E-6.

The following examples will further illustrate the invention without, however, limiting it thereto.

A. 4-(Py-Y)-1,2-benzenediamines

A-1. 4-(4-Pyridinyl)-1,2-benzenediamine—A mixture containing 115 g. of 4-(4-amino-3-nitrophenyl)pyridine, 1100 ml. of acetic acid and 1.2 g. of platinum oxide was shaken at room temperature under hydrogen under catalytic hydrogenation conditions until the required amount (1.5 mole) of hydrogen was taken up. The catalyst was filtered off and the filtrate concentrated in vacuo under reduced pressure. The residue was titrated with aqueous ammonium hydroxide to liberate the free base form of the product which was recrystallized from ethanol to yield 50.4 g. of 4-(4-pyridinyl)-1,2-benzenediamine, m.p. 260°-267° C. with decomposition.

A-2. 4-(4-Pyridinyl)-1,2-benzenediamine—A mixture containing 8 g. of 4-(4-acetylamino-3-nitrophenyl)pyridine, 40 ml. of concentrated hydrochloric acid, 15 ml. of ethanol and 27 g. of stannous chloride dihydrate was stirred for 30 minutes at room temperature and then heated on a steam bath for four hours. The reaction mixture was cooled in an ice bath and the separated solid was collected. The solid was suspended in water and the mixture was basic by adding 35% aqueous sodium hydroxide solution. The yellow solid precipitate was collected, washed with water and dried to yield 3.60 g. of 4-(4-pyridinyl)-1,2-benzenediamine, m.p. 255°-258° C. A mixed melting point of this compound and the product obtained above in Example A-1 showed no depression.

A-3. 4-(4-Pyridinyl)-1,2-benzenediamine—To a stirred solution containing 27 g. of stannous dichloride dihydrate, 40 ml. of concentrated hydrochloric acid and 15 ml. of ethanol was added 7.2 g. of 4-(3-acetylamino-4-nitrophenyl)pyridine and the resulting mixture was stirred while heating on a steam bath for two hours and then allowed to stand at room temperature overnight (about fifteen hours). The solid was collected and then treated with 35% aqueous sodium hydroxide solution with stirring for about fifteen minutes. The yellow solid was collected from the resulting mixture to yield 3.4 g. of 4-(3,4-diaminophenyl)pyridine, m.p. 245°-250.3° C. The mass spectra data of this compound obtained by the above procedure is consistent with that of 4-(4-pyridinyl)-1,2-benzenediamine.

The above intermediate 4-(3-acetylamino-4-nitrophenyl)pyridine was prepared by the following procedure: To 65 ml. of ice cold 90% $HNO_3$ was added slowly with stirring 16.5 g. of 3-(4-pyridinyl)acetanilide so that the temperature of the reaction mixture did not rise above 5° C. The reaction mixture was maintained below this temperature for six hours and then poured into ice cold water. The resulting mixture was made basic with ammonium hydroxide and the mixture then acidified with acetic acid. The resulting light yellow solid was collected, washed with water, dried and crystallized from ethanol to produce 9.2 g. of 4-(3-acetylamino-4-nitrophenyl)pyridine, m.p. 175°-177° C.

A-4. 4-(2,6-Dimethyl-4-pyridinyl)-1,2-benzenediamine, 48.4 g. as its dimethanesulfonate, m.p. 255°-258° C., was prepared following the procedure described in Example A-1 using 34 g. of 4-(3-amino-4-nitrophenyl)-2,6-dimethyl pyridine, 200 ml. of acetic acid and 1 g. of platinum oxide, and converting the diamine base in isopropyl alcohol to its dimethanesulfonate with excess methanesulfonic acid.

4-(3-Amino-4-nitrophenyl)-2,6-dimethylpyridine was prepared in two steps by first nitrating (with 45 ml. of concentrated nitric acid) 10 g. of 3-(2,6-dimethyl-4-pyridinyl)acetanilide using the procedure given above in the second paragraph of Example A-3 to produce 5.2 g. of 4-(3-acetylamino-4-nitrophenyl)-2,6-dimethylpyridine and hydrolyzing the latter compound (41.2 g.) with 6 N aqueous hydrochloric acid to produce 4-(3-amino-4-nitrophenyl)-2,6-dimethylpyridine (34.2 g.), m.p. 226°–229° C.

Following the two step procedure described in Example A-3 but using in place of 3-(4-pyridinyl)acetanilide a molar equivalent quantity of the appropriate 3-(PY)acetanilide, it is contemplated that there can be obtained successively the corresponding 3(4 or 5)-(3-acetylamino-4-nitrophenyl)pyridines and 4-(Py)-1,2-benzenediamines respectively of Examples A-5 through A-11.

A-5. 3-(3-Acetylamino-4-nitrophenyl)pyridine and 4-(3-pyridinyl)-1,2-benzenediamine, using 3-(3-pyridinyl)acetanilide.

A-6. 4-(3-Acetylamino-4-nitrophenyl)-2-methylpyridine and 4-(2-methyl-4-pyridinyl)-1,2-benzenediamine, using 3-(2-methyl-4-pyridinyl)acetanilide.

A-7. 5-(3-Acetylamino-4-nitrophenyl)-2-methylpyridine and 4-(2-methyl-5-pyridinyl)-1,2-benzenediamine, using 3-(2-methyl-5-pyridinyl)acetanilide.

A-8. 4-(3-Acetylamino-4-nitrophenyl)-2,6-diethylpyridine and 4-(2,6-diethyl-4-pyridinyl)-1,2-benzenediamine, using 3-(2,6-diethyl-4-pyridinyl)acetanilide.

A-9. 4-(3-Acetylamino-4-nitrophenyl)-2-ethylpyridine and 4-(2-ethyl-4-pyridinyl)-1,2-benzenediamine, using 3-(2-ethyl-4-pyridinyl)acetanilide.

A-10. 4-(3-Acetylamino-4-nitrophenyl)-2,3-dimethylpyridine and 4-(2,3-dimethyl-4-pyridinyl)-1,2-benzenediamine, using 3-(2,3-dimethyl-4-pyridinyl)acetanilide.

A-11. 4-[(4-Pyridinyl)methyl]-1,2-benzenediamine, m.p. 156°–158° C., 13.9 g. was obtained following the procedure described in Example A-1 using 20 g. of 4-[(4-amino-3-nitrophenyl)methyl]pyridine, 250 ml. of acetic acid and 0.40 g. of platinum oxide.

The above intermediate, 4-[(4-amino-3-nitrophenyl)methyl]pyridine was prepared in several steps as follows: Two portions, 25 g. and 15.26 g. of 4-(4-nitrobenzyl)pyridine were catalytically hydrogenated (75 and 45 minutes respectively) at room temperature using in each instance 250 ml. of acetic acid and 0.40 g. of platinum oxide, filtering off the catalyst in each, combining the filtrates, concentrating in vacuo, dissolving the residue in water, making the aqueous solution alkaline with ammonium hydroxide, collecting the precipitate, recrystallizing the solid from isopropyl alcohol (final volume of 100 ml. and drying the recrystallized material in vacuo at 70° C. for 60 hours to yield 26.5 g. of 4-[(4-aminophenyl)methyl]pyridine, m.p. 157.5°–159° C., which was acetylated using 80 ml. of acetic anhydride and 160 ml. of chloroform to produce 25 g. of 4-[(4-acetylaminophenyl)methyl]pyridine, m.p. 172°–173.5° C., in turn, nitrated as above (second paragraph of Example A-3) using 120 ml. of 90% nitric acid and recrystallizing the nitrated product with isopropyl alcohol-water to produce 17.64 g. of 4-[(4-acetylamino-3-nitrophenyl)methyl]pyridine, m.p. 156°–157.5° C. 4-[(4-Amino-3-nitrophenyl)methyl]pyridine, m.p. 150°–151.5° C., 14.1 g., was obtained by refluxing with stirring for three hours a mixture containing 16.9 g. of 4-[(4-acetylamino-3-nitrophenyl)methyl]pyridine, 17.3 g. of potassium hydroxide, 270 ml. of ethanol and 110 ml. of water, chilling the reaction mixture, collecting the precipitated product and drying it at 90° C. for more than six hours. Then, following the procedure described above in Example A-1 using 20 g. of 4-[(4-amino-3-nitrophenyl)methyl]pyridine, 250 ml. of acetic acid and 0.40 g. of platinum oxide, there was obtained 13.9 g. of 4-[(4-pyridinyl)methyl]-1,2-benzenediamine, m.p. 156°–158° C.

B. 5-(Py-Y)-1H-benzimidazol-2-ols

B-1. 5-(4-Pyridinyl)-1H-benzimidazol-2-ol—A mixture containing 11.1 g. of 4-(4-pyridinyl)-1,2-benzenediamine, 22.5 g. of urea and 200 ml. of dimethylformamide was refluxed with stirring for about five hours. The reaction mixture was treated with some decolorizing charcoal, the mixture filtered, the filtrate concentrated to a volume of about 150 ml. and then diluted with water. The resulting precipitate was collected, recrystallized from dimethylformamide-water and dried in vacuo at 80° C. for sixteen hours and then in vacuo at 95° C. for another sixteen hours to yield 10 g. of 5-(4-pyridinyl)-1H-benzimidazol-2-ol, m.p. 345°–348° C.

A 9.14 g. sample of 5-(4-pyridinyl)-1H-benzimidazol-2-ol was dissolved in dimethylformamide and the solution treated with excess hydrogen chloride in ethanol. The mixture was diluted with ethyl acetate, the precipitate was collected and dried at 90° C. in vacuo for about sixteen hours to yield 8.39 g. of 5-(4-pyridinyl)-1H-benzimidazol-2-ol hydrochloride, m.p. >365° C.

Other acid-addition salts of 5-(4-pyridinyl)-1H-benzimidazol-2-ol are conveniently prepared by adding to a mixture of 2 g. of 5-(4-pyridinyl)-1H-benzimidazol-2-ol in about 40 ml. of aqueous methanol the appropriate acid, e.g., methanesulfonic acid, concentrated sulfuric acid, concentrated phosphoric acid, to a pH of about 2 to 3, filling the mixture after partial evaporation and collecting the precipitated salt, e.g., methanesulfonate, sulfate, phosphate, respectively. Also, the acid-addition salt is conveniently prepared in aqueous solution by adding to water with stirring molar equivalent quantities each of 5-(4-pyridinyl)-1H-benzimidazol-2-ol and the appropriate acid, e.g., lactic acid or hydrochloric acid, to prepare respectively the monolactate or monohydrochloride salt in aqueous solution.

B-2. 5-(4-Pyridinyl)-1H-benzimidazol-2-ol N(py)oxide—To a solution containing 10.56 g. of 5-(4-pyridinyl)-1H-benzimidazol-2-ol in 400 ml. of acetic acid was added dropwise with stirring over a period of about 2 hours at about 45°–50° C. a solution containing 16.25 g. of 85% m-chloroperoxybenzoic acid in 150 ml. of acetic acid. The reaction mixture was then stirred for about 3½ hours at about 45°–50° C. and then concentrated in vacuo to a volume of about 100–150 ml. The remaining material was added to water. The solid was collected, slurried with dilute potassium carbonate solution, the mixture filtered and the collected solid recrystallized from acetic acid-water and dried at 85°–90° in vacuo over 60 hours to yield 8.26 g. of light tan solid, m.p. 331°–335° C. The solid was then recrystallized from dimethylformamide and first dried as above and then dried a second time at 120° C. in vacuo for about 18 hours to yield 5.11 g. of product. The product along with another 3 g. of material prepared in another run were combined, taken up in dilute potassium hydroxide solution with warming, the solution filtered thru diatomaceous earth and the filtrate was treated with acetic acid. The product that separated was collected, dried at 90° C. in a vacuum oven for about 60 hours to yield 7.64 g. of 5-(4-pyridinyl)-1H-benzimidazol-2-ol N(py)oxide containing ⅓ H₂O as confirmed by its nuclear magnetic resonance spectrum and its elemental analysis for C, H and N.

B-3. 5-[(4-Pyridinyl)methyl]-1H-benzimidazol-2-ol hydrochloride, m.p. 262°–269° C., 8.43 g., was prepared following the procedure described above in Example B-3 using 13.54 g. of 4-[(4-pyridinyl)methyl]benzene-1,2-diamine, 24.9 g. of urea, 200 ml. of dimethylformamide and conversion of the resulting 5-[(4-pyridinyl)methyl]-1H-benzimidazol-2-ol in methanol by adding excess hydrogen chloride in ether to produce its corresponding hydrochloride salt.

Following the procedure described above in Example B-1 but using in place of 4-(4-pyridinyl)-1,2-benzenediamine a molar equivalent quantity of the appropriate 5-(Py-Y)-1,2-benzenediamine, it is contemplated that there can be obtained respectively the corresponding 5-(Py-Y)-1H-benzimidazol-2-ols of Examples B-4 and B-10.

B-4. 5-(3-Pyridinyl)-1H-benzimidazol-2-ol, using 4-(3-pyridinyl)-1,2-benzenediamine.

B-5. 5-(2-Methyl-4-pyridinyl)-1H-benzimidazol-2-ol, using 4-(2-methyl-4-pyridinyl)-1,2-benzenediamine.

B-6. 5-(2-Methyl-5-pyridinyl)-1H-benzimidazol-2-ol, using 4-(2-methyl-5-pyridinyl)-1,2-benzenediamine.

B-7. 5-(2,6-Dimethyl-4-pyridinyl)-1H-benzimidazol-2-ol, using 4-(2,6-dimethyl-4-pyridinyl)-1,2-benzenediamine.

B-8. 5-(2,6-Diethyl-4-pyridinyl)-1H-benzimidazol-2-ol, using 4-(2,6-diethyl-4-pyridinyl)-1,2-benzenediamine.

B-9. 5-(2-Ethyl-4-pyridinyl)-1H-benzimidazol-2-ol, using 4-(2-ethyl-4-pyridinyl)-1,2-benzenediamine.

B-10. 5-(2,3-Dimethyl-4-pyridinyl)-1H-benzimidazol-2-ol, using 4-(2,3-dimethyl-4-pyridinyl)-1,2-benzenediamine.

C. 5-(Py-Y)-1H-benzimidazole-2-thiols

C-1. 5-(4-Pyridinyl)-1H-benzimidazole-2-thiol—A mixture containing 11.1 g. of 4-(4-pyridinyl)-1,2-benzenediamine, 10.58 g. of potassium ethylxanthate, 250 ml. of ethanol and 25 ml. of water was stirred under reflux for about 10 hours. To the partially cooled reaction mixture was added another 3.21 g. of potassium ethyl xanthate and the resulting reaction mixture was stirred under reflux for another 4 hours and then allowed to stand at room temperature overnight. The reaction mixture was filtered and the filtrate diluted with water up to a volume of about 700 ml. The diluted filtrate was acidified with acetic acid and the resulting acidic solution chilled. The separated solid was collected, recrystallized from methanol, dried at 80° C. over 60 hours, recrystallized from dimethylformamide-water and dried at 80° C. in a vacuum oven for 18 hours and then at 90°–95° C. in vacuo for over 5 hours to produce 11.36 g. of 5-(4-pyridinyl)-1H-benzimidazole-2-thiol, m.p. 296°->310° C.

In another run following the above procedure and using the same quantities of reactants, the product obtained was dissolved in 250 ml. of warm dimethylformamide and the resulting solution was treated with excess methanesulfonic acid in ethanol (0.02 N); and, the warm suspension was stirred, allowed to cool and then diluted with ether. The separated product was collected, dried at 90° C. in a vacuum over for about 11 hours to yield 13 g. of 5-(4-pyridinyl)-1H-benzimidazole-2-thiol methanesulfonate, m.p. >315° C.

Other acid-addition salts of 5-(4-pyridinyl)-1H-benzimidazole-2-thiol are conveniently prepared by adding to a mixture of 2 g. of 5-(4-pyridinyl)-1H-benzimidazole-2-thiol in about 40 ml. of aqueous methanol the appropriate acid, e.g., concentrated sulfuric acid, concentrated phosphoric acid, to a pH of about 2 to 3, chilling the mixture after partial evaporation and collecting the precipitated salt, e.g., sulfate, phosphate, respectively. Also, the acid-addition salt is conveniently prepared in aqueous solution by adding to water with stirring molar equivalent quantities each of 5-(4-pyridinyl)-1H-benzimidazole-2-thiol and the appropriate acid, e.g., lactic acid or hydrochloric acid, to prepare respectively the monolactate or monohydrochloride salt in aqueous solution.

Following the procedure described in Example C-1 but using in place of 4-(4-pyridinyl)-1,2-benzenediamine a molar equivalent quantity of the appropriate 4-(Py-Y)-1,2-benzenediamine, it is contemplated that there can be obtained respectively the corresponding 5-(Py-Y)-1H-benzimidazole-2-thiols of Examples C-2 thru C-9.

C-2. 5-(3-Pyridinyl)-1H-benzimidazole-2-thiol, using 4-(3-pyridinyl)-1,2-benzenediamine.

C-3. 5-(2-Methyl-4-pyridinyl)-1H-benzimidazole-2-thiol, using 4-(2-methyl-4-pyridinyl)-1,2-benzenediamine.

C-4. 5-(2-Methyl-5-pyridinyl)-1H-benzimidazole-2-thiol, using 4-(2-methyl-5-pyridinyl)-1,2-benzenediamine.

C-5. 5-(2,6-Dimethyl-4-pyridinyl)-1H-benzimidazole-2-thiol, using 4-(2,6-dimethyl-4-pyridinyl)-1,2-benzenediamine.

C-6. 5-(2,6-Diethyl-4-pyridinyl)-1H-benzimidazole-2-thiol, using 4-(2,6-diethyl-4-pyridinyl)-1,2-benzenediamine.

C-7. 5-(2-Ethyl-4-pyridinyl)-1H-benzimidazole-2-thiol, using 4-(2-ethyl-4-pyridinyl)-1,2-benzenediamine.

C-8. 5-(2,3-Dimethyl-4-pyridinyl)-1H-benzimidazole-2-thiol, using 4-(2,3-dimethyl-4-pyridinyl)-1-2-benzenediamine.

C-9. 5-[(4-Pyridinyl)methyl]-1H-benzimidazole-2-thiol, using 4-[(4-pyridinyl)methyl]-1,2-benzenediamine.

D. 5-(Py-Y)-1H-Benzimidazole-2-ol Lower-alkyl Ethers

D-1. 2-Ethoxy-5-(4-pyridinyl)-1H-benzimidazole—A mixture containing 13.5 g. of 4-(4-pyridinyl)-1,2-benzenediamine, 90 ml. of tetraethoxymethane and 3 ml. of acetic acid was stirred at room temperature for 2 hours and then on a steam bath for about 2 hours and 15 minutes. The reaction mixture was filtered thru diatomaceous earth and the filtrate concentrated in vacuo to yield a brown gummy material. The residual gummy material was washed twice with ether, suspended in water and the aqueous mixture made alkaline with dilute potassium bicarbonate solution. The resulting brown precipitate was collected, washed with water and recrystallized by dissolving it in hot acetone, treating the acetone solution with decolorizing charcoal and filtering, and treating the filtrate with water. The aqueous acetone mixture was allowed to cool, was then chilled whereupon the product separated. The product was collected, dried in vacuo at 50° C. for 18 hours over sodium hydroxide to yield 10.55 g. of 2-ethoxy-5-(4- pyridinyl)-1H-benzimidazole monohydrate, m.p. 104°–110° C.

Acid-addition salts of 2-ethoxy-5-(4-pyridinyl)-1H-benzimidazole are conveniently prepared by adding to a mixture of 2 g. of 2-ethoxy-5-(4-pyridinyl)-1H-benzimidazole in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., methanesulfonate, sulfate, phosphate, respectively. Also, the acid-addition salt is conveniently prepared in aqueous solution by adding to water with stirring molar equivalent quantities each of 2-ethoxy-5-(4-pyridinyl)-1H-benzimidazole and the appropriate acid, e.g., lactic acid or hydrochloric acid, to prepare respectively a monolactate or monohydrochloride salt in aqueous solution.

Following the procedure described in Example D-1 but using in place of 4-(4-pyridinyl)-1,2-benzenediamine a molar equivalent quantity of the appropriate 4-(Py-Y)-1,2-benzenediamine, it is contemplated that there can be obtained the corresponding respective 2-ethoxy-5-(Py-Y)-1H-benzimidazoles of Examples D-2 thru D-9.

D-2. 2-Ethoxy-5-(3-pyridinyl)-1H-benzimidazole, using 4-(3-pyridinyl)-1,2-benzenediamine.

D-3. 2-Ethoxy-5-(2-methyl-4-pyridinyl)-1H-benzimidazole, using 4-(2-methyl-4-pyridinyl)-1,2-benzenediamine.

D-4. 2-Ethoxy-5-(2-methyl-5-pyridinyl)-1H-benzimidazole, using 4-(2-methyl-5-pyridinyl)-1,2-benzenediamine.

D-5. 2-Ethoxy-5-(2,6-dimethyl-4-pyridinyl)-1H-benzimidazole, using 4-(2,6-dimethyl-4-pyridinyl)-1,2-benzenediamine.

D-6. 2-Ethoxy-5-(2,6-diethyl-4-pyridinyl)-1H-benzimidazole, using 4-(2,6-diethyl-4-pyridinyl)-1,2-benzenediamine.

D-7. 2-Ethoxy-5-(2-ethyl-4-pyridinyl)-1,2-benzenediamine, using 4-(2-ethyl-4-pyridinyl)-1,2-benzenediamine.

D-8. 2-Ethoxy-5-(2,3-dimethyl-4-pyridinyl)-1H-benzimidazole, using 4-(2,3-dimethyl-4-pyridinyl)-1,2-benzenediamine.

D-9. 2-Ethoxy-5-[(4-pyridinyl)methyl]-1H-benzimidazole, using 4-[(4-pyridinyl)methyl]-1,2-benzenediamine.

Following the procedure described in Example D-1 but using in place of tetraethoxymethane, i.e., tetraethyl orthocarbonate, a molar equivalent quantity of the appropriate tetra-(lower-alkoxy)methane, i.e., tetra-(lower-alkyl) orthocarbonate, it is contemplated that there can be obtained the corresponding respective 2-(lower-alkoxy)-5-(4-pyridinyl)-1H-benzimidazole of Examples D-10 through D-13.

D-10. 2-Methoxy-5-(4-pyridinyl)-1H-benzimidazole, using tetramethoxymethane.

D-11. 2-n-Propoxy-5-(4-pyridinyl)-1H-benzimidazole, using tetra-n-propoxymethane.

D-12. 2-n-Butoxy-5-(4-pyridinyl)-1H-benzimidazole, using tetra-n-butoxymethane.

D-13. 2-n-Hexoxy-5-(4-pyridinyl)-1H-benzimidazole, using tetra-n-hexoxymethane, i.e., tetra-n-hexyl orthocarbonate.

E. 5-(Py-Y)-1H-benzimidazole-2-thiol Lower-alkyl Thioethers

E-1. 2-(Ethylthio)-5-(4-pyridinyl)-1H-benzimidazole—Following the procedure described above in Example C-1 using the same quantities of reactants, there was obtained the reaction mixture containing in solution 5-(4-pyridinyl)-1H-benzimidazol-2-thiol as its potassium salt. To this reaction mixture was added 4.6 ml. of ethyl bromide and the resulting mixture was stirred for 5 hours at room temperature. There was then added another 4.6 ml. of ethyl bromide and the mixture was stirred for an additional 30 minutes at room temperature and then allowed to stand over the weekend. The reaction mixture was filtered thru diatomaceous earth and the filtrate concentrated in vacuo. The remaining residue was suspended in water and the aqueous suspension was acidified with excess acidic acid followed by the addition of a small quantity of dilute hydrochloric acid. The insoluble solid was filtered off and the acidic filtrate was neutralized with 10% potassium bicarbonate solution to yield 11.1 g. of solid which was recrystallized from isopropyl alcohol-ethyl acetate and then dried in a vacuum oven at 80° C. for 16 hours to yield 3.87 g. of 2-(ethylthio)-5-(4-pyridinyl)-1H-benzimidazole as its hydrobromide salt, m.p. 302°–310° C.

2-(Ethylthio)-5-(4-pyridinyl)-1H-benzimidazole in free base form is obtained by treating an aqueous-ethanolic solution of its hydrobromide salt with aqueous sodium hydroxide, removing the ethanol in vacuo and collecting said free base form by filtration.

Other acid-addition salts of 2-(ethylthio)-5-(4-pyridinyl)-1H-benzimidazole are conveniently prepared by adding to a mixture of 1 g. of 2-(ethylthio)-5-(4-pyridinyl)-1H-benzimidazole in about 20 ml. of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring molar equivalent quantities each of 2-(ethylthio)-5-(4-pyridinyl)-1H-benzimidazole and the appropriate acid, e.g., lactic acid or hydrochloric acid, to prepare respectively the lactate or hydrochloride in aqueous solution.

Following the procedure described in Example E-1 but using in place of 5-(4-pyridinyl)-1H-benzimidazole-2-thiol a molar equivalent quantity of the corresponding appropriate 5-(Py-Y)-1H-benzimidazole-2-thiol and corresponding appropriate lower-alkylating agent in place of ethyl bromide, it is contemplated that there can be obtained the corresponding 2-(lower-alkylthio)-5-(Py-Y)-1H-benzimidazoles respectively of Examples E-2 thru E-7.

E-2. 2-Methylthio-5-(3-pyridinyl)-1H-benzimidazole, using 5-(3-pyridinyl)-1H-benzimidazole-2-thiol and methyl iodide.

E-3. 2-n-Propylthio-5-(2-methyl-4-pyridinyl)-1H-benzimidazole, using 5-(2-methyl-4-pyridinyl)-1H-benzimidazole-2-thiol and n-propyl bromide.

E-4. 2-Isopropylthio-5-(2-methyl-5-pyridinyl)-1H-benzimidazole, using 5-(2-methyl-5-pyridinyl)-1H-benzimidazole-2-thiol and isopropyl iodide.

E-5. 2-n-Butylthio-5-(2,6-dimethyl-4-pyridinyl)-1H-benzimidazole, using 5-(2,6-dimethyl-4-pyridinyl)-1H-benzimidazole-2-thiol and n-butyl bromide.

E-6. 2-n-Hexylthio-5-(2-ethyl-4-pyridinyl)-1H-benzimidazole, using 5-(2-ethyl-4-pyridinyl)-1H-benzimidazole-2-thiol and n-hexyl chloride.

E-7. 2-Ethylthio-5-[(4-pyridinyl)methyl]-1H-benzimidazole, using 5-[(4-pyridinyl)methyl]-1H-benzimidazole-2-thiol and ethyl bromide.

The usefulness of the compounds of formula I or salts thereof as cardiotonic agent is demonstrated by their effectiveness in standard pharmacological test procedures, for example, in causing a significant increase in contractile force of the isolated cat atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat atria and papillary muscle procedure, the compounds of formula I or pharmaceutically-acceptable acid-addition salts thereof at doses of 3, 10, 30, and/or 100 μg./ml., were found to cause significant increases, that is, greater than 25% in papillary muscle force and significant increases, that is, greater than 25%, in right atrial force, while causing a lower percentage increase (about one-half or less than the percentage increase in right atrial force or papillary muscle force) in right atrial rate. For example, when tested at said dose levels by this procedure, the following preferred compounds were found to cause increases of 30 to 200% in papillary muscle force and/or right atrial force: the compounds of Examples B-1, B-2, B-3, C-1, D-1 and E-1.

When tested by said anesthetized dog procedure, the compounds of formula I or pharmaceutically-acceptable acid-addition salts thereof at doses of 1.0, 3.0 and/or 10 mg./kg. administered intravenously were found to cause significant increases, that is, 25% or greater, in cardiac contractile force or cardiac contractility with lower changes in heart rate and blood pressure. For example, when tested at one or more of said dose levels by this procedure, the following compounds were found to cause increases of 28 to 174% in contractile force and lower changes in heart rate and blood pressure: the compounds of Examples B-2, B-3, D-1 and E-1.

The present invention includes within its scope a cardiotonic composition for increasing cardiac contractility, said composition comprising a pharmaceutically-acceptable carrier and, as the active component thereof, a cardiotonically-effective amount of the compound of formula I or pharmaceutically-acceptable acid-addition salt thereof. The invention also includes within its scope the method for increasing cardiac contractility in a patient requiring such treatment which comprises administering to such patient a cardiotonically-effective amount of said compound of formula I or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and perserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, perserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. 5-(Py-Y)-1H-benzimidazol-2-ol or 5-(Py-Y)-1H-benzimidazole-2-thiol or lower-alkyl ether or thioether thereof having the formula

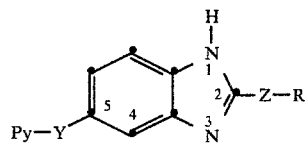

where Z is O or S, Y is a direct linkage or lower-alkylene having one or two carbon atoms, R is hydrogen or lower-alkyl, and Py is 4- or 3-pyridinyl or 4- or 3-pyridinyl having one or two lower-alkyl substituents or 1-oxide thereof, or pharmaceutically-acceptable acid-addition salt thereof.

2. A compound according to claim 1 where Py is 4- or 3-pyridinyl, Y is a direct linkage or methylene, and R is hydrogen, methyl or ethyl.

3. 5-(4-Pyridinyl)-1H-benzimidazol-2-ol according to claim 2.

4. 5-(4-Pyridinyl)-1H-benzimidazol-2-ol N(py)oxide according to claim 1.

5. 5-[(4-Pyridinyl)methyl]-1H-benzimidazol-2-ol according to claim 2.

6. 5-(4-Pyridinyl)-1H-benzimidazole-2-thiol according to claim 2.

7. 2-Ethoxy-5-(4-pyridinyl)-1H-benzimidazole according to claim 2.

8. 2-(Ethylthio)-5-(4-pyridinyl)-1H-benzimidazole according to claim 2.

9. A cardiotonic composition for increasing cardiac contractility, said composition comprising a pharmaceutically-acceptable inert carrier and, as the active component thereof, a cardiotonically-effective amount of 5-(Py-Y)-1H-benzimidazol-2-ol, 5-(Py-Y)-1H-benzimidazole-2-thiol or lower-alkyl ether or thioether thereof or pharmaceutically-acceptable acid-addition salt thereof, where Z is O or S, Y is a direct linkage or lower-alkylene having one or two carbon atoms, R is hydrogen or lower-alkyl, and Py is 4- or 3-pyridinyl or 4- or 3-pyridinyl having one or two lower-alkyl substituents or 1-oxide thereof.

10. A composition according to claim 9 where Py is 4- or 3-pyridinyl, Y is a direct linkage or methylene, and R is hydrogen, methyl or ethyl.

11. The method for increasing cardiac contractility in a patient requiring such treatment which comprises administering to such patient a cardiotonically-effective amount of 5-(Py-Y)-1H-benzimidazol-2-ol, 5-(Py-Y)-1H-benzimidazole-2-thiol or lower-alkyl ether or thioether thereof or pharmaceutically-acceptable acid-addition salt thereof, where Z is O or S, Y is a direct linkage or lower-alkylene having one or two carbon atoms, R is hydrogen or lower-alkyl, and Py is 4- or 3-pyridinyl or 4- or 3-pyridinyl having one or two lower-alkyl substituents or 1 oxide thereof.

12. The method according to claim 11 where Py is 4- or 3-pyridinyl, Y is a direct linkage or methylene, and R is hydrogen, methyl or ethyl.

* * * * *